United States Patent
Griffin et al.

(10) Patent No.: US 10,456,152 B2
(45) Date of Patent: Oct. 29, 2019

(54) CATHETER WITH A COLLECTION CHAMBER

(71) Applicant: Cook Medical Technologies LLC, Bloomington, IN (US)

(72) Inventors: Dennis J. Griffin, Englewood, CO (US); Ram H. Paul, Jr., Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 895 days.

(21) Appl. No.: 14/962,086

(22) Filed: Dec. 8, 2015

(65) Prior Publication Data

US 2016/0157873 A1 Jun. 9, 2016

Related U.S. Application Data

(60) Provisional application No. 62/089,648, filed on Dec. 9, 2014.

(51) Int. Cl.

| | |
|---|---|
| *A61B 17/221* | (2006.01) |
| *A61M 1/36* | (2006.01) |
| *A61B 17/22* | (2006.01) |
| *A61M 39/06* | (2006.01) |
| *A61M 1/00* | (2006.01) |

(52) U.S. Cl.
CPC ............ *A61B 17/221* (2013.01); *A61B 17/22* (2013.01); *A61M 39/0613* (2013.01); *A61B 2017/2215* (2013.01); *A61B 2017/22038* (2013.01); *A61B 2017/22079* (2013.01); *A61B 2217/005* (2013.01); *A61M 1/0056* (2013.01); *A61M 2039/0673* (2013.01)

(58) Field of Classification Search
CPC .......... A61B 17/22; A61B 2017/22079; A61B 2217/005; A61M 39/0613; A61M 2039/062; A61M 2039/0673; A61M 1/0056

See application file for complete search history.

(56) References Cited

U.S. PATENT DOCUMENTS

| | | | |
|---|---|---|---|
| 5,827,229 A | 10/1998 | Auth et al. | |
| 8,057,497 B1 * | 11/2011 | Raju | A61B 17/22 604/22 |
| 2005/0137498 A1 | 6/2005 | Sakal et al. | |
| 2006/0129091 A1 | 6/2006 | Bonnette et al. | |
| 2009/0036871 A1 | 2/2009 | Hayase et al. | |
| 2013/0317529 A1 * | 11/2013 | Golden | A61B 10/0275 606/159 |
| 2014/0081075 A1 * | 3/2014 | Salama | A61M 25/0017 600/31 |

* cited by examiner

*Primary Examiner* — Katherine M Rodjom
(74) *Attorney, Agent, or Firm* — Brinks Gilson & Lione (57) ABSTRACT

A catheter is provided with a collection chamber located between a seal and a cap. The seal is located distal from the collection chamber, and the cap is located proximal from the collection chamber. The seal may be opened and closed to alternately allow the passage of material into the collection chamber and prevent fluid from escaping from the shaft lumen. The cap may be opened and closed to allow the removal of a mass from the collection chamber and to prevent fluid from escaping during collection of the mass.

20 Claims, 7 Drawing Sheets

CATHETER WITH A COLLECTION CHAMBER

CROSS REFERENCE TO RELATED APPLICATIONS

This application claims the benefit of U.S. Provisional Application No. 62/089,648 filed on Dec. 9, 2014, the entire contents of which is hereby incorporated by reference.

BACKGROUND

The present invention relates generally to medical devices and more particularly to a catheter for removing non-liquid material from a patient, such as a clot, thrombus or embolus from a vein.

One medical condition that affects a large number of patients is the formation of internal clots, thrombi and emboli within the vasculature. Some medical sources distinguish clots from thrombi and emboli. For example, a clot can be considered to be the initial stage of blood coagulation where blood forms a non-liquid mass due to reduced blood flow or other physiological conditions. A thrombus can be considered to be a more fibrous state of a clot where platelets and other cells aggregate to form a more solid mass. Oftentimes, a thrombus occurs where the collagen layer of a vessel becomes exposed since blood exposure to collagen encourages a cascade of clotting activity. However, numerous other factors can also encourage thrombus formation, such as hemodialysis grafts and certain drug treatments. A thrombus is generally considered to be a clotted mass that remains attached to a vessel wall, and is typically considered to be an embolus when the thrombus breaks loose from the vessel wall and flows through the vasculature. This can cause serious conditions because an embolus will often flow along the vasculature to a point where it obstructs downstream tissues, which can starve the obstructed tissues of blood and oxygen.

The seriousness of clotting formation and related events can vary from relatively minor conditions that are generally recoverable and/or treatable to life-threatening situations. For example, if the clotting involved is a short-term event and the individual is healthy, the vasculature may clear naturally without medical intervention. Hemodialysis patients with artificial fistulas may also suffer from thrombus formation within the fistula, which may require treatment or the surgical introduction of a new fistula. Deep vein thrombosis is another condition that can affect blood circulation within a patient's legs. This condition can start with mild symptoms of discomfort in the leg, but if left untreated thrombus formation can propagate throughout the patient's venous system and result in a life-threatening situation.

A number of methods for treating clots, thrombi and emboli have been tried. One method involves inserting a catheter so that the distal end of the catheter is close to the clot, thrombus or emboli. Suction is then applied to the lumen of the catheter to aspirate the vessel and suck the mass into the catheter and out of the vessel. However, the devices that are available for this treatment have various disadvantages. One concern is that any blood escaping from the catheter during use of the device should be minimized to reduce blood loss during the procedure. In addition, it can be difficult to remove non-liquid masses, like clots, thrombi and emboli, from conventional catheters that are not designed for this purpose.

Accordingly, the inventors believe that an improved catheter with a collection chamber for the removal of a non-liquid mass from a patient would be desirable.

SUMMARY

A catheter is described with a seal and a collection chamber for removing non-liquid masses, such as clots, thrombi and emboli, from a patient's body while minimizing the risk of blood loss during the procedure. The catheter has a cap located proximal from the first seal that may be closed while the mass is aspirated into the collection chamber. The collection chamber is located between the cap and the first seal. During aspiration, the first seal is open to allow passage of the mass into the collection chamber. The first seal may then be closed to prevent fluid from escaping from the shaft lumen, and the cap is opened to permit removal of the mass. The cap may then be closed and the first seal reopened to collect additional masses. The inventions herein may also include any other aspect described below in the written description, the claims, or in the attached drawings and any combination thereof.

BRIEF DESCRIPTION OF SEVERAL VIEWS OF THE DRAWINGS

The invention may be more fully understood by reading the following description in conjunction with the drawings, in which.

DETAILED DESCRIPTION

Figure 1:
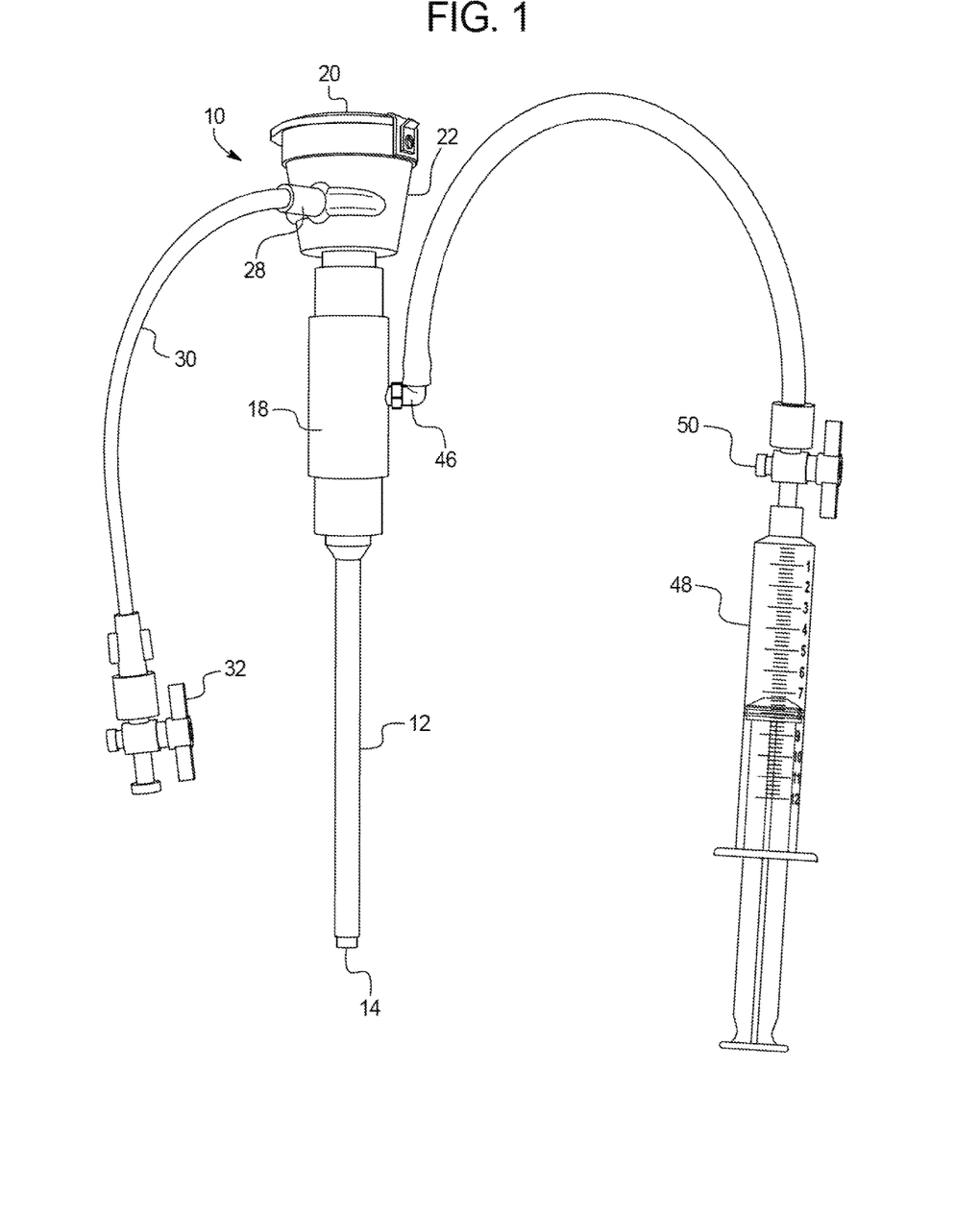
FIG. 1 is an elevational view of a catheter.
Figure 6:
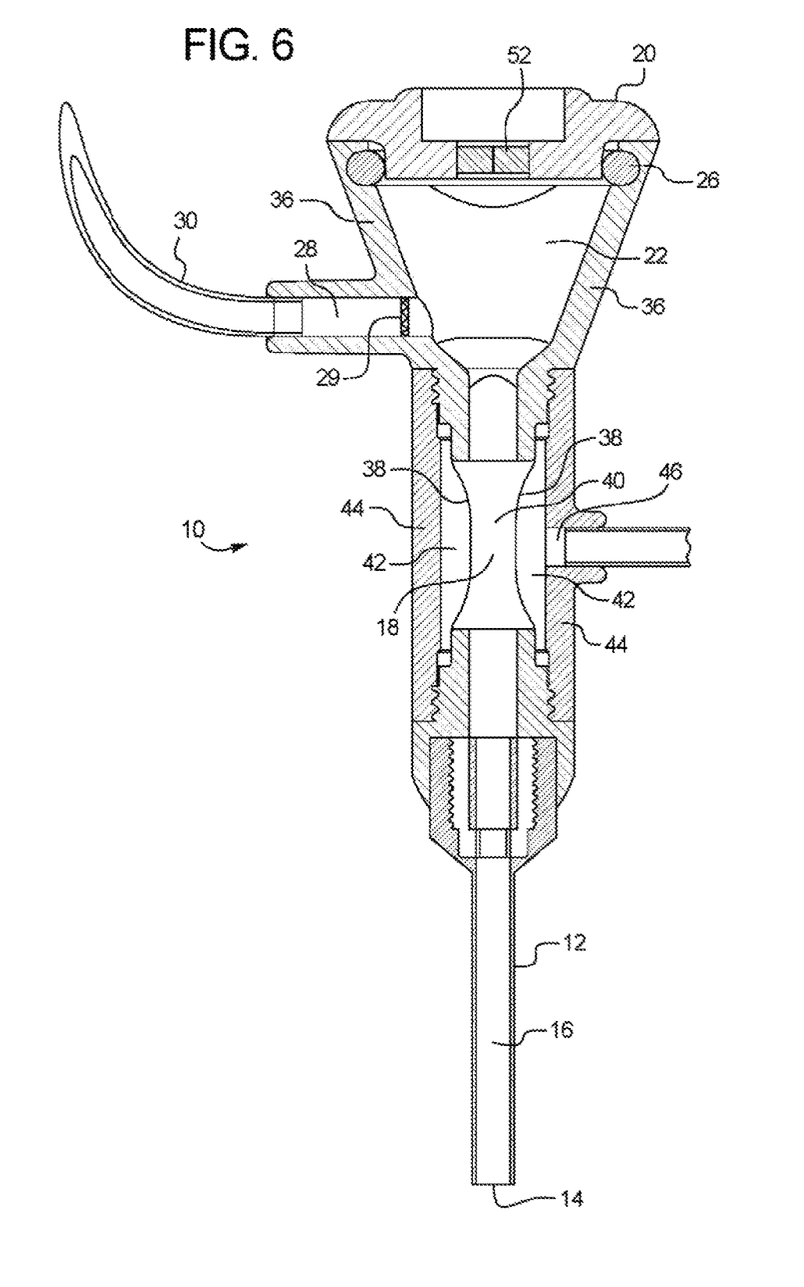
FIG. 6 is a cross-sectional view of the catheter, showing the cap closed and the first seal opened.
Figure 7:
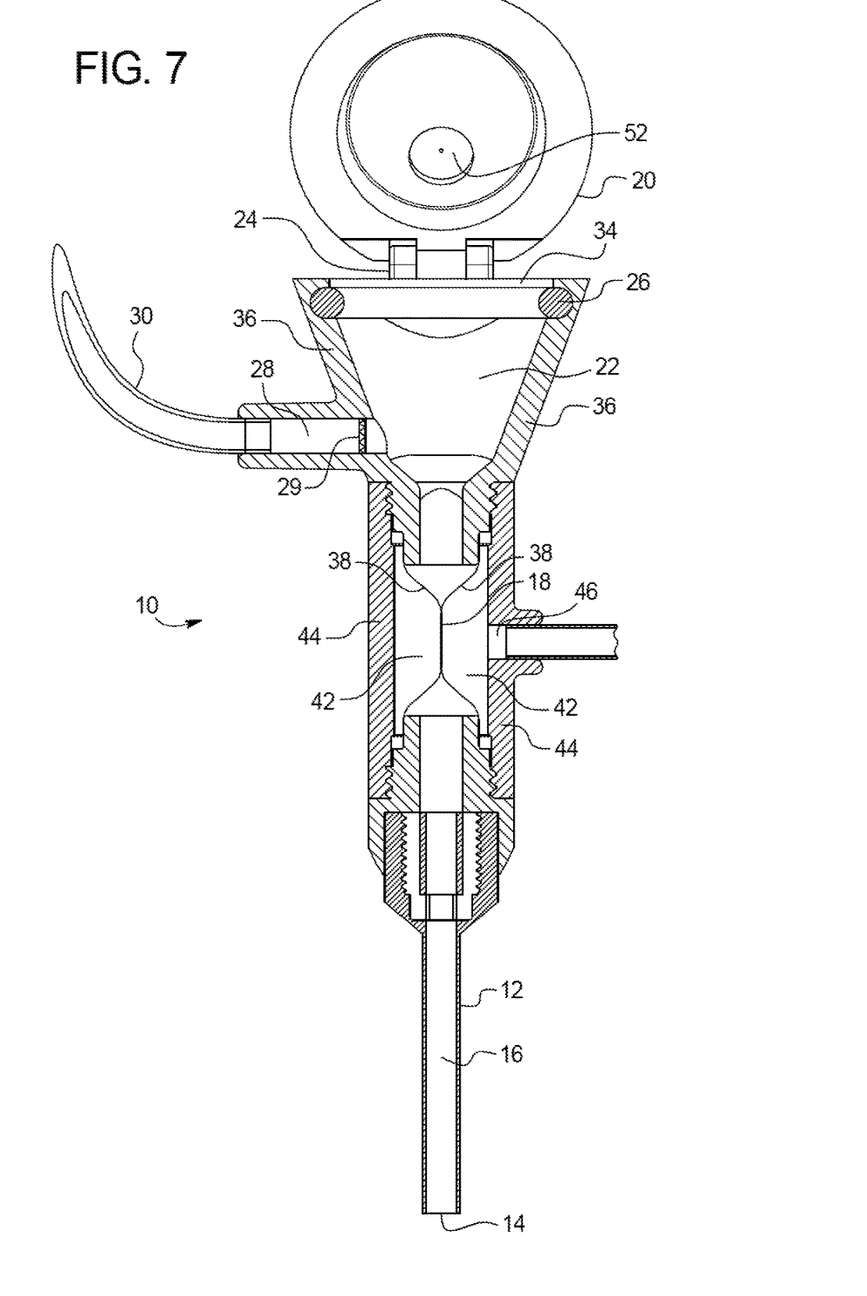
FIG. 7 is a cross-sectional view of the catheter, showing the cap opened and the first seal closed.

Referring now to the figures, and particularly to FIG. 1, a catheter 10 is shown for collecting non-liquid masses, such as clots, thrombi, emboli or other masses. The catheter 10 is preferably used for collecting non-liquid masses from the vasculature and in particular the venous system. Thus, the catheter 10 is provided with a shaft 12 that extends through an access site into a patient's body. The access site typically provides access to the venous system, and the shaft 12 will extend through a vein so that the distal opening 14 of the shaft 12 is located next to the mass intended to be collected. Preferably, the shaft 12 is made of a flexible material like nylon or other polymers so that the shaft 12 can conform to the path of the vessel. The distal end of the shaft 12 is preferably atraumatic so that damage to the vessel wall is minimized. As illustrated in FIGS. 6-7, the shaft 12 is hollow with a lumen 16 extending from the distal opening 14 to the proximal portion of the catheter 10.

Along the proximal portion, the catheter 10 includes a first seal 18 that is capable of being closed to prevent fluid in the shaft lumen 16 from passing through the first seal 18 and escaping. Preferably, the first seal 18 can be actively controlled by the user so that the seal 18 can be actuated between a closed state and an open state. That is, the physician is able to open the first seal 18 and close the first seal 18 from outside the catheter 10 without pushing a device through the first seal 18. The first seal 18 may thus be thought of as a type of valve that can be closed to prevent fluid from escaping and opened when desired to allow the passage of medical devices and the mass to be collected.

Figure 2:
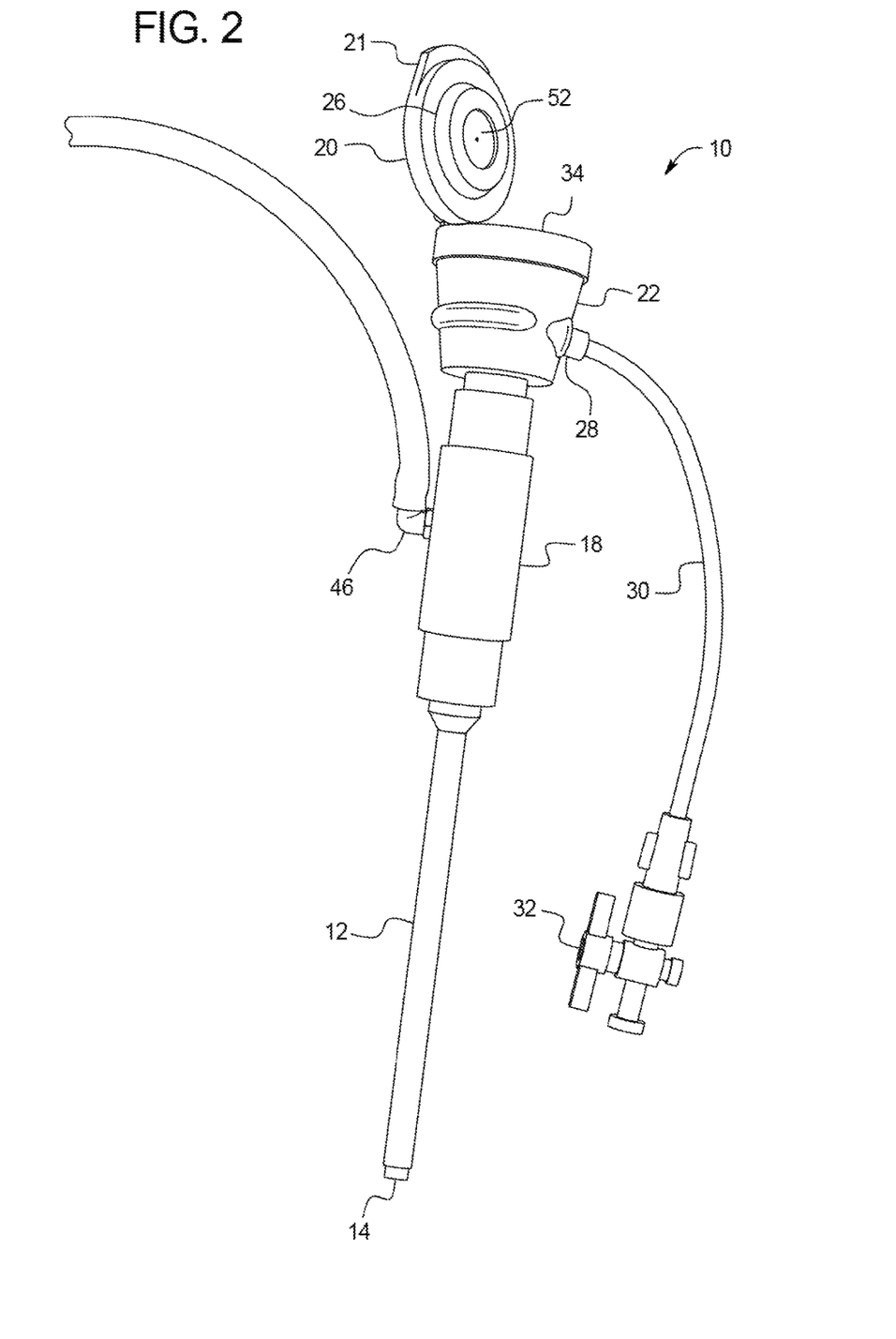
FIG. 2 is an elevational view of the catheter with the cap open.

A cap 20 is located proximally from the first seal 18, and a collection chamber 22 is defined between the cap 20 and the first seal 18. In FIG. 1, the cap 20 is shown closed so that the cap 20 prevents fluid from escaping from the catheter 10. However, as shown in FIG. 2, the cap 20 may be opened to provide access to the collection chamber 22. Preferably, the cap 20 is attached to the catheter 10 with a hinge 24 so that the cap 20 is not removable from the catheter 10. This allows the physician to open and close the cap 20 as desired without concern for dropping or misplacing the cap 20, which could make the cap 20 unsterile or could risk excessive blood loss. The cap 20 also preferably has a lip 21 that extends outward from the outer surface of the collection chamber 22 to allow the physician to easily grasp the cap 20 to open it. While the cap 20 may be oriented in various ways as desired, it is preferable for the cap 20 to extend across the axis of the catheter shaft 12 when it is closed. This allows straight access into the collection chamber 22 when the cap 20 is open to retrieve a collected mass. As shown in FIG. 6, a snap 26, such as an o-ring 26 or other detent, may also be provided to keep the cap 20 closed and prevent the cap 20 from inadvertently opening. The snap 26 may also help in sealing the cap 20 when it is closed to prevent fluid like blood from escaping from the outside of the cap 20.

Figure 5:
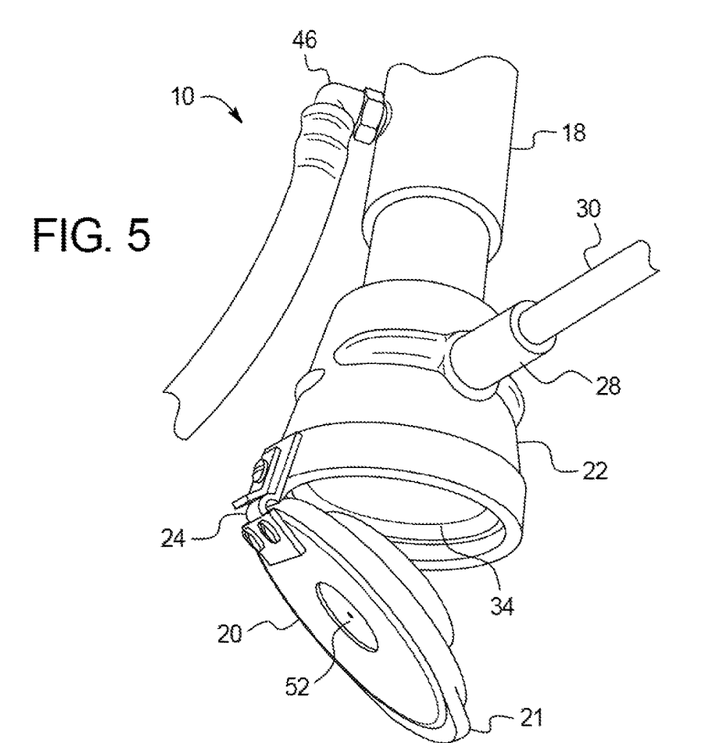
FIG. 5 is an end view of the catheter, showing the cap opened.

In use, suction is applied to a suction port 28 that is located along the collection chamber 22. As shown in FIG. 1, a hose 30 may be attached to the suction port 28, and a valve 32 may be provided on the hose 30 if desired to open and close communication with the suction port 28. Various suction sources, such as a syringe or a vacuum machine, may be attached to the hose 30 or valve 32. While suction is being applied to the suction port 28, the cap 20 is preferably closed and the first seal 18 is open as illustrated in FIG. 6. As a result, blood and the mass intended to be collected passes through the distal opening 14 in the shaft 12 and through the shaft lumen 16. Since the first seal 18 is open, the material also passes through the first seal 18 and is received within the collection chamber 22. As shown in FIGS. 6-7, it may be desirable to provide a filter 29 in or adjacent to the suction port 28 to prevent the non-liquid mass from passing through the suction port 28. At this stage, the suction source may be shut off or the valve 32 closed to stop further suctioning. In order to remove the mass from the collection chamber 22, the first seal 18 is closed to prevent any additional fluid from escaping during the removal step. As illustrated in FIGS. 5 and 7, the cap 20 may now be opened without being concerned about additional blood escaping from the lumen 16 of the shaft 12. The material collected within the collection chamber 22 may then be removed through the cap opening 34. If desired, forceps may be inserted through the cap opening 34 into the collection chamber 22 to grasp the mass and pull it out of the collection chamber 22. Once the mass has been removed, the cap 20 may be closed, the first seal 18 opened, and suction applied to the suction port 28 again to collect additional material. This process may be repeated as needed to collect as much material as desired during the procedure. Between each collection step, the catheter shaft 12 may be moved through the vessel to relocate the distal opening 14 next to each mass intended to be collected.

Figure 8:
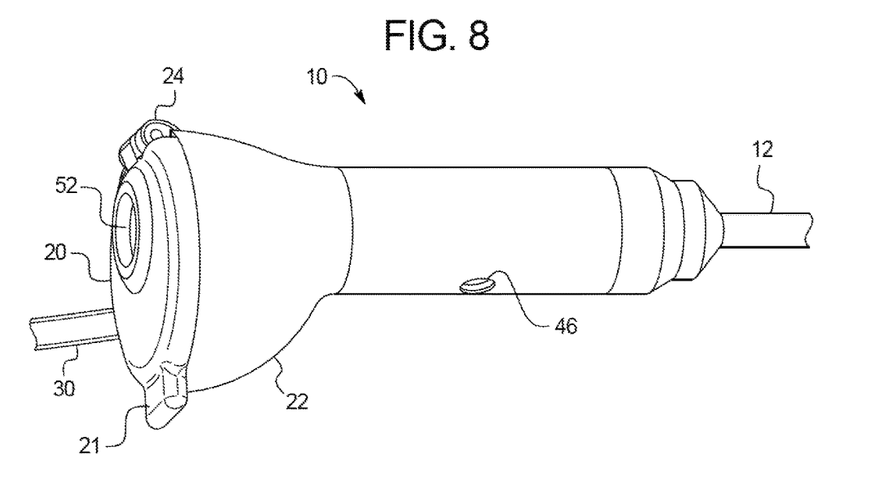
FIG. 8 is a perspective view of another embodiment of the catheter, showing the cap closed.
Figure 9:
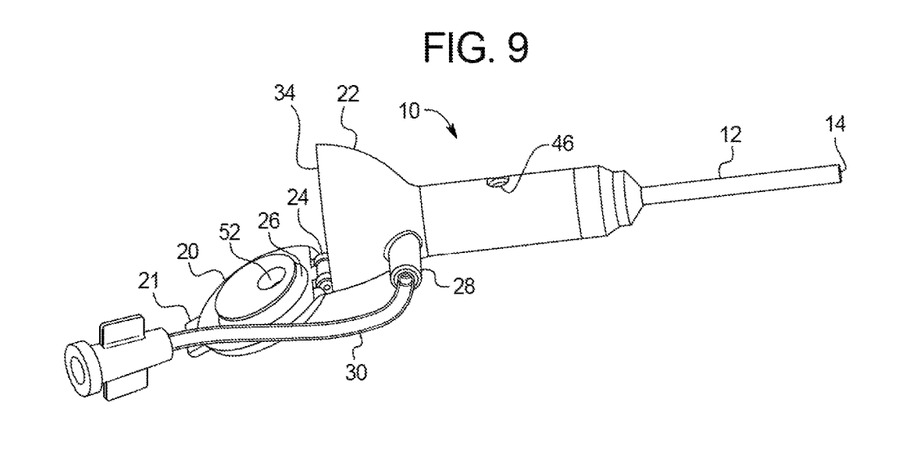
FIG. 9 is a perspective view of the embodiment of FIG. 8, showing the cap opened.

The collection chamber 22 will preferably be of a sufficient size to collect a non-liquid mass, such as a clot, thrombus or embolus. Thus, the collection chamber 22 preferably has a cross-sectional area that is larger than the cross-sectional area of the shaft lumen 16. The cap opening 34 is also preferably large enough to insert forceps to grasp the collected material. Thus, the cap opening 34 preferably has a diameter of 10 mm to 30 mm. The collection chamber 32 is preferably also an elongate chamber 22 along the length of the axis of the shaft 12 so that passage through the cap opening 34, collection chamber 22 and shaft lumen 16 is generally straight. However, the collection chamber 22 need not be perfectly coaxial with the shaft lumen 16 and may have an offset shape as shown in FIGS. 8-9. The suction port 28 preferably extends from a side wall 36 of the collection chamber 22 so that the port 28 extends angularly from the chamber 22 with respect to the axis of the chamber 22. Thus, the suction port 28 does not interfere with the straight passage of the mass through the shaft lumen 16, first seal 18, collection chamber 22 and cap opening 34. Although the size of the collection chamber 22 may vary depending on the particular use of the device, a volume of 1 cc to 10 cc may be preferred to collect typical clots, thrombi and emboli. The length of the collection chamber 22 between the first seal 18 and the cap 20 is also preferably 5 mm to 50 mm.

Figure 3:
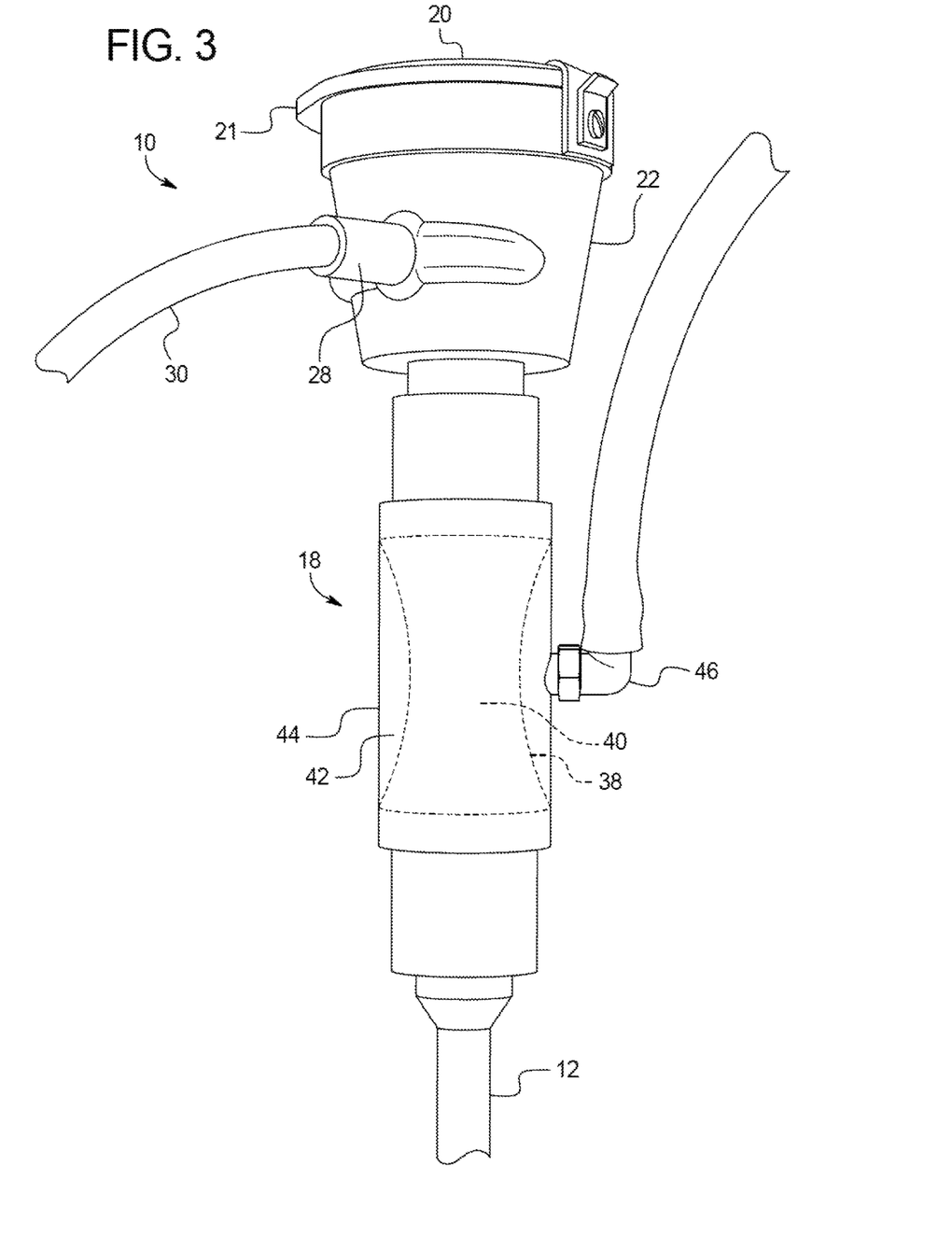
FIG. 3 is an enlarged elevational view of the proximal portion of the catheter.
Figure 4:
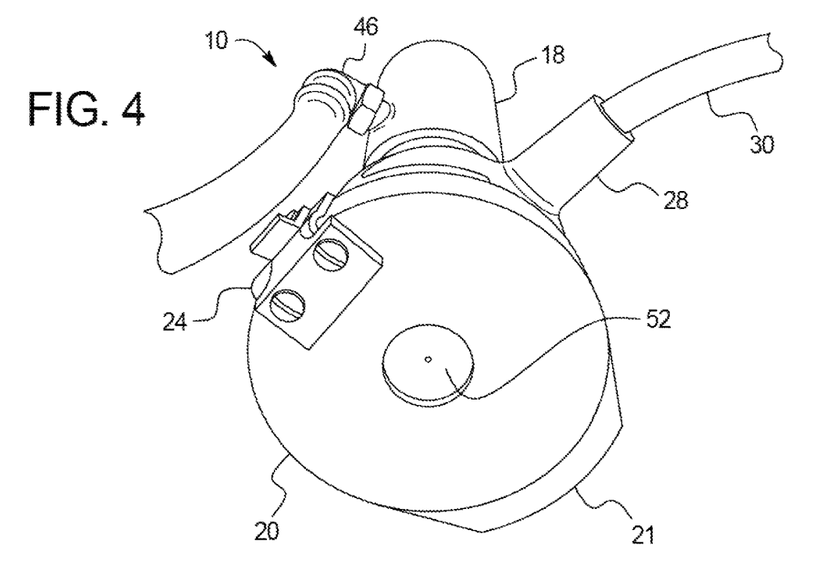
FIG. 4 is an end view of the catheter, showing the cap closed.

Although various types of seals 18 are possible for the first seal 18, one type of seal 18 that may be used for the first seal 18 is illustrated in FIGS. 3 and 6-7. This type of seal 18 may have a bladder 38 that circumferentially surrounds a lumen 40 passing between the shaft lumen 16 and the collection chamber 22. The bladder 38 is typically made from a thin material 38 that can flex and squeeze in upon itself as illustrated in FIG. 7 to close the seal 18. The bladder 38 may also flex outward to open the passageway 40 between the shaft lumen 16 and the collection chamber 22 as illustrated in FIG. 6. Movement of the bladder 38 between the closed state and the opened state is controlled by pressure in the pressure chamber 42 between the outer surface of the bladder 38 and an outer wall 44 of the first seal 18. The outer wall 44 may be provided with a pressure port 46 to apply pressure to the pressure chamber 42 to control opening and closing of the bladder 38. As shown in FIG. 1, a syringe 48 and a valve 50 may be connected to the pressure port 46 to apply pressure to the pressure chamber 42, and pressure may be retained to keep the first seal 18 closed by closing the valve 50. Although less desirable, other types of seals may also be used for the first seal 18, such as a seal with an elastic member that is directly squeezed by twisting an outer housing. A ball valve may also be used for the first seal 18.

It may also be desirable to provide a second seal 52 in the cap 20. The second seal 52 may be generally aligned with the lumen 16 of the shaft 12 to allow medical devices to extend through the catheter 10 while the cap 20 is closed. Thus, in the design of FIGS. 8-9, the second seal 52 is off-center in the cap 20 so that the second seal 52 is coaxial with the shaft lumen 16, since the collection chamber 22 is offset. For example, in typical intraluminal procedures, access to the vasculature will first be obtained using a guidewire that extends through the overlapping tissues and into a vein or artery. The proximal portion of the guidewire remains outside of the patient to provide a pathway through the patient's tissues into the vein or artery. Once access has been gained with a guidewire, the distal opening 14 may be threaded onto the guidewire, and the catheter 10 may be slid onto the guidewire so that the guidewire extends through the shaft lumen 16, the first seal 18, the collection chamber 22 and the second seal 52. The catheter 10 may then be threaded over the guidewire until the shaft 12 is located within the vein or artery. The guidewire may then be withdrawn from the catheter 10 by pulling the guidewire proximally through the second seal 52. During this stage of the procedure, the first seal 18 preferably remains open so that the first seal 18 does not interfere with passage of the guidewire. Since the cap 20 remains closed during introduction of the catheter 10 into the vasculature and the second seal 52 seals against the guidewire, blood will not escape even if the first seal 18 is open. Unlike the first seal 18, the second seal 52 may be a non-actuable seal 52, in that the second seal 52 passively seals and does not need to be separately controlled between an opened and closed state. Thus, the second seal 52 may be biased toward the closed state. Where the second seal 52 is passive, it is preferable for the second seal 52 to be bidirectional so that it seals both when suction is applied to the collection chamber 22 and when blood pressure exists in the collection chamber 22. Thus, as shown in FIG. 6, the second seal 52 extends perpendicular to the axis of the shaft lumen 16 and is not biased in either the proximal or distal direction.

While preferred embodiments of the inventions have been described, it should be understood that the inventions are not so limited, and modifications may be made without departing from the inventions herein. While each embodiment described herein may refer only to certain features and may not specifically refer to every feature described with respect to other embodiments, it should be recognized that the features described herein are interchangeable unless described otherwise, even where no reference is made to a specific feature. It should also be understood that the advantages described above are not necessarily the only advantages of the inventions, and it is not necessarily expected that all of the described advantages will be achieved with every embodiment of the inventions. The scope of the inventions is defined by the appended claims, and all devices and methods that come within the meaning of the claims, either literally or by equivalence, are intended to be embraced therein.

What is claimed is:

1. A catheter for removing a non-liquid mass from a body, comprising:
    a shaft comprising a lumen extending therethrough in communication with a distal opening defined by the shaft, the shaft being adapted to extend through an access site into a patient's body;
    a first seal in communication with said lumen of said shaft, said first seal being actuable between a closed state and an open state, said closed state preventing fluid flow therethrough and said open state allowing said non-liquid mass to pass therethrough;
    a collection chamber disposed proximally from said first seal and being in communication with said first seal, said collection chamber being adapted to receive said non-liquid mass;
    an openable cap disposed proximally from said collection chamber and being in communication with the collection chamber, said cap preventing fluid flow therethrough in a closed state and allowing said non-liquid mass to pass therethrough in an open state;
    a suction port in communication with said collection chamber, said suction port being adapted to draw said non-liquid mass through said lumen and said first seal into said collection chamber; and
    a second seal in said cap, said second seal being a non-actuable seal that is biased towards a closed state, wherein the second seal passively seals and does not need to be separately controlled between an opened and closed state;
    wherein said first seal is actuable to said closed state while said cap is in said open state, said non-liquid mass thereby being removable from said collection chamber while fluid is prevented from escaping said lumen by said first seal.

2. The catheter according to claim 1, wherein said cap is attached to said catheter with a hinge, said cap thereby being non-removable.

3. The catheter according to claim 1, further comprising a snap retaining said cap in said closed state.

4. The catheter according to claim 1, wherein said cap extends across an axis of said shaft in said closed state.

5. The catheter according to claim 1, wherein said second seal is adapted to allow a guidewire to pass therethrough and prevent fluid flow therethrough.

6. The catheter according to claim 5, wherein said second seal is bidirectional and seals in response to pressure and suction.

7. The catheter according to claim 1, wherein a volume of said collection chamber is 1 cc to 10 cc.

8. The catheter according to claim 1, wherein a length of said collection chamber is 5 mm to 50 mm.

9. The catheter according to claim 1, wherein a cross-sectional area of said collection chamber is larger than a cross-sectional area of said lumen.

10. The catheter according to claim 1, wherein said collection chamber is elongated along an axis of said shaft.

11. The catheter according to claim 1, wherein said first seal comprises a bladder and a pressure chamber, said bladder closing in said closed state in response to pressure within said pressure chamber and opening in said open state in response to releasing said pressure from within said pressure chamber.

12. The catheter according to claim 1, wherein said port extends angularly from said collection chamber with respect to an axis thereof.

13. The catheter according to claim 1, further comprising a filter preventing said non-liquid mass from passing through said suction port.

14. The catheter according to claim 1, wherein a volume of said collection chamber is 1 cc to 10 cc, and said cap is attached to said catheter with a hinge, said cap thereby being non-removable.

15. The catheter according to claim 14, further comprising a second seal in said cap, said second seal adapted to allow a guidewire to pass therethrough and prevent fluid flow therethrough.

16. The catheter according to claim 15, wherein said collection chamber is elongated along an axis of said shaft, and said port extends angularly from said collection chamber with respect to an axis thereof.

17. The catheter according to claim 16, further comprising a snap retaining said cap in said closed state, said second seal is a non-actuable seal, and said second seal is bidirectional and seals in response to pressure and suction, and a cross-sectional area of said collection chamber is larger than a cross-sectional area of said lumen.

18. The catheter according to claim 1, wherein said cap is attached to said catheter with a hinge, said cap thereby being non-removable, further comprising a snap retaining said cap in said closed state, a cross-sectional area of said collection chamber is larger than a cross-sectional area of said lumen, and said port extends angularly from said collection chamber with respect to an axis thereof.

19. The catheter according to claim 18, wherein said cap extends across an axis of said shaft in said closed state, further comprising a second seal in said cap, said second seal adapted to allow a guidewire to pass therethrough and prevent fluid flow therethrough, said second seal is bidirectional and seals in response to pressure and suction, a volume of said collection chamber is 1 cc to 10 cc, a length of said collection chamber is 5 mm to 50 mm, said collection chamber is elongated along said axis of said shaft, said first seal comprises a bladder and a pressure chamber, said bladder closing in said closed state in response to pressure within said pressure chamber and opening in said open state in response to releasing said pressure from within said pressure chamber, and further comprising a filter preventing said non-liquid mass from passing through said suction port.

20. A method of removing a clot, thrombus, or embolus from a vein, comprising:

inserting a catheter through an access site into a patient's vein, said catheter comprising a shaft with a lumen extending therethrough, a first seal in communication with said lumen, a collection chamber disposed proximally from said first seal and in communication with said first seal, an openable cap disposed proximally from said collection chamber and in communication with said collection chamber, a second non-actuable seal biased towards a closed state disposed in the cap, and a suction port in communication with said collection chamber, said cap being closed with a guidewire extending through said lumen, said first seal, said collection chamber, and said second seal;

removing said guidewire from said catheter by withdrawing said guidewire proximally through said lumen, said first seal, said collection chamber, and said second seal;

applying suction pressure to said suction port, said first seal being open, and said clot, thrombus or embolus passing through said lumen and said first seal and being received within said collection chamber;

closing said first seal to prevent blood flow from said lumen into said collection chamber; and opening said cap and removing said clot, thrombus, or embolus from said collection chamber.

* * * * *